US009084839B2

(12) United States Patent
Contrada

(10) Patent No.: US 9,084,839 B2
(45) Date of Patent: Jul. 21, 2015

(54) ADHESIVE FOR USE ON SKIN

(71) Applicant: Berry Plastics Corporation, Evansville, IN (US)

(72) Inventor: Svetlana I Contrada, Manalapan, NJ (US)

(73) Assignee: Berry Plastics Corporation, Evansville, IN (US)

( * ) Notice: Subject to any disclaimer, the term of this patent is extended or adjusted under 35 U.S.C. 154(b) by 232 days.

(21) Appl. No.: 13/851,256

(22) Filed: Mar. 27, 2013

(65) Prior Publication Data

US 2013/0260134 A1 Oct. 3, 2013

Related U.S. Application Data

(60) Provisional application No. 61/616,260, filed on Mar. 27, 2012.

(51) Int. Cl.
| | |
|---|---|
| A61F 13/02 | (2006.01) |
| A61L 24/06 | (2006.01) |
| C09J 133/04 | (2006.01) |
| C09J 139/06 | (2006.01) |
| A61L 24/04 | (2006.01) |
| C09J 133/02 | (2006.01) |
| C09J 133/06 | (2006.01) |
| A61L 15/58 | (2006.01) |

(52) U.S. Cl.
CPC ............ *A61L 24/043* (2013.01); *A61L 15/585* (2013.01); *C09J 133/02* (2013.01); *C09J 133/064* (2013.01); *Y10T 428/2891* (2015.01)

(58) Field of Classification Search
None
See application file for complete search history.

(56) References Cited

U.S. PATENT DOCUMENTS

| | | | |
|---|---|---|---|
| 4,370,380 A | 1/1983 | Shah | |
| 5,645,855 A * | 7/1997 | Lorenz | 424/449 |
| 7,691,404 B2 * | 4/2010 | Song et al. | 424/448 |
| 2011/0314706 A1 | 12/2011 | French et al. | |

FOREIGN PATENT DOCUMENTS

EP  1329225 A2  7/2003

OTHER PUBLICATIONS

PCT International Search Report and Written Opinion established by ISA/EP on Jun. 17, 2013 and issued in connection with PCT/US2013/034096.

* cited by examiner

*Primary Examiner* — Vu A Nguyen
(74) *Attorney, Agent, or Firm* — Barnes & Thornburg LLP

(57) ABSTRACT

An adhesive for use on skin comprises acid-functionalized polyacrylate, one or more polyvinylpyrrolidones, and a low softening point resin.

18 Claims, 4 Drawing Sheets

ADHESIVE FOR USE ON SKIN

PRIORITY CLAIM

This application claims priority under 35 U.S.C. §119(e) to U.S. Provisional Application Ser. No. 61/616,260, filed Mar. 27, 2012, which is expressly incorporated by reference herein.

BACKGROUND

The present disclosure relates to an adhesive. More particularly, the present disclosure relates to an adhesive that may be used with medical devices such as skin patches and transdermal delivery devices.

SUMMARY

An adhesive in accordance with the present disclosure, which adhesive may be used with a medical device, is polyacrylate-based and pressure-sensitive. Illustratively, the adhesive may provide sustainable adhesion, minimal slippage, and high cohesive strength.

In illustrative embodiments, an adhesive in accordance with the present disclosure comprises acid-functionalized polyacrylate, one or more polyvinylpyrrolidones, and a low softening point resin.

In illustrative embodiments, a device may be equipped with an adhesive as described herein. The adhesive may be coated on a device, which device may be in the form of a pad, film, foam or other suitable carrier (substrate), that is approved for medical applications.

Additional features of the present disclosure will become apparent to those skilled in the art upon consideration of the following detailed description of illustrative embodiments exemplifying the best mode of carrying out the disclosure as presently perceived.

BRIEF DESCRIPTION OF THE DRAWINGS

The detailed description particularly refers to the accompanying figures in which.

DETAILED DESCRIPTION

Figure 1A:
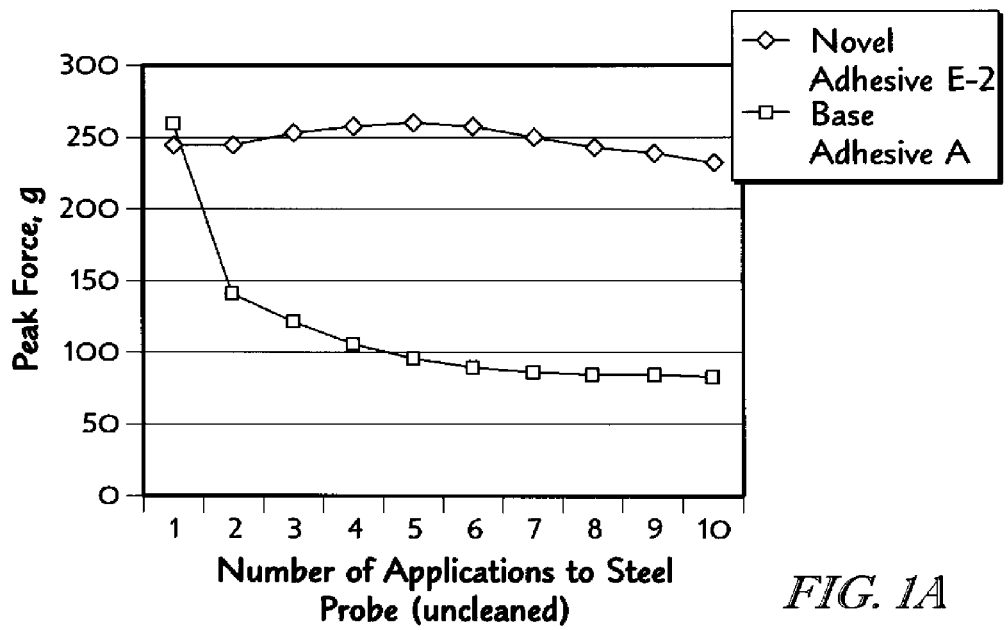
FIG. 1A is a graph showing peak force data recorded for an exemplary (novel) adhesive-bearing device that has been reapplied multiple times onto the same uncleaned surface of a steel probe.

Illustrative embodiments of the present disclosure relate to pressure-sensitive adhesives comprising acid-functionalized polyacrylate and to pressure-sensitive articles equipped with such adhesives.

A first illustrative embodiment includes an adhesive for use on skin that comprises polyacrylate prepared from monomers of acrylic acid and acrylic or meth(acrylic) esters, one or more polyvinylpyrrolidones, and a low softening point resin. The adhesive can be a blend of polymers and copolymers that is free, or substantially free, of cross-linking prior to the application of the adhesive onto a substrate (e.g., a device). Illustratively, the adhesive exhibits a peel adhesion to steel of from about 0.2 lb/linear inch to about 4 lb/linear inch, which is a useful range for applications on skin.

A polyacrylate suitable for use in an illustrative embodiment of the present disclosure includes a polymer in which the primary components are monomers of acrylic acid and acrylic or meth(acrylic) esters; such polymers are also referred to as acrylic adhesives. Commercial medical and transdermal grade polyacrylates are available from Henkel (DURO-TAK® 129A, DURO-TAK® 1154), Ashland (Aroset™ 5488, Aroset™ 280) or Cytec (GMS 737 and GMS 738). In illustrative examples, the amount of polyacrylate in an adhesive in accordance with the present disclosure may be between about 60% and 92% by weight, or preferably between about 70% and 80% by weight.

Polyvinylpyrrolidone (hereinafter "PVP") or mixtures of polyvinylpyrrolidones (hereinafter "PVPs") suitable for use in an illustrative embodiment can be or include a water-soluble polymer prepared from monomers of N-vinylpyrrolidone. PVPs may have a weight average molecular weight (Mw, g/mol) as determined by light scattering of between about 2,000 g/mol and about 1,500,000 g/mol, and K-values from about 10.2 to about 96.3. Commercially available grades of PVPs are suitable for use in the adhesives described herein. For example, PVP grades such as Kollidon® 12 PF (MW 2,000-3,000 g/mol, K-value of 10.2-13.8), Kollidon® 25 (MW 28,000-34,000 g/mol and K-value of 22.5-27.0), and Kollidon® 90F (MW 1,000,000-1,500,000 g/mol and K-value of 81.0-96.3) produced by BASF may be used. Other commercially available grades of PVP are also suitable for use. The amount of PVP in the adhesive may be between about 3% and about 20% by weight, or preferably between about 5% and about 10% by weight. The molecular weight of PVP(s) in the adhesive may exert noticeable effects on the adhesive properties of a polyacrylate mixed therewith. PVP(s) can be dissolved upon mixing solvents, such as ethyl alcohol, after which they may be mixed into a polyacrylate adhesive. In one illustrative example, a PVP may have a molecular weight of about 28,000 g/mol.

In another illustrative embodiment, an adhesive in accordance with the present disclosure may include a low softening point resin that increases the tack or stickiness of the adhesive to a surface (e.g., skin). Such resins may be low-molecular weight compounds that do not substantially change the glass transition temperature, Tg, of a base polymer. Further, such resins may be present in the adhesive at about 5% to about 20% by weight. Useful resins include, for example, copolymers of acrylamide and ethylhexyl acrylate; for example, a relatively low molecular weight product from polymerization of a mixture of 20%-80% acrylamide and 20%-80% ethylhexyl acrylate. The aforementioned resins have a number-average molecular weight (Mn) range between 15,400 and 31,790 g/mol, a weight-average molecular weight (Mw) between 80,300 and 96,500 g/mol, and a degree of polydispersity in the range of 2.9-6.0 as determined by gel permeation chromatography (GPC) using polystyrene standards.

In illustrative examples, low softening point resins included in an adhesive as described herein have a Tg below minus 30° C., a B&R Melt Point between 70-80° C., and a relatively low molecular weight. The low softening point of such resins provides cold flow at room temperature, which can rheologically enhance the final formulation by improving flow properties of the adhesive when applied to skin at body temperature and thereby enabling improved wettability of skin. A low softening point resin may be supplied in polymerized form as an acrylic-based polymer in a conventional solvent (such as toluene, methyl ethyl ketone (MEK), isopropyl alcohol (IPA), and like solvents or in a solvent blend). Alternatively, a low softening point resin may be a solid material that may be dissolved in ethyl acetate or other solvent in order to enable homogeneous mixing with acrylic polymers.

An illustrative example of a low softening point resin available for use in an adhesive in accordance with the present disclosure is Acrynax 4326 manufactured by Franklin Adhesives and Polymers. Desirable low softening point resins, such as Acrynax 4326, may include about 40 weight percent of acrylamide and about 60 weight percent of ethylhexyl acrylate. Illustratively, a low softening point resin may be present in an adhesive in accordance with the present disclosure in about 5 to 20 weight percent, or preferably between about 5 to 10 weight percent.

In another illustrative embodiment, an adhesive in accordance with the present disclosure may be a pressure sensitive adhesive, which refers to a viscoelastic material that adheres instantaneously to most substrates with the application of very slight pressure and which remains permanently tacky. A polymer is a pressure-sensitive adhesive when it has the properties of a pressure-sensitive adhesive per se or functions as a pressure-sensitive adhesive upon admixture with resins, plasticizers and/or other additives. In illustrative examples, blended adhesive compositions of the present disclosure are solvent-based with viscosity ranging from about 1,500 to about 25,000 centipoise (cps) at ambient temperatures.

In another illustrative embodiment, an adhesive in accordance with the present disclosure may be directly coated or transfer coated onto a device, such as a pad, film, foam or other suitable carrier (substrate) that is approved for medical application. The thickness of the adhesive may be between about 1 and 7 mils, between about 2 and 5 mils, or between about 3 and 4 mils. The adhesive may be dried in an oven to reduce solvent and may be exposed to higher temperatures to cure the base acrylic adhesive, which can provide a desired degree of cohesive strength.

In another illustrative embodiment, an adhesive in accordance with the present disclosure can remain on skin for a desired period of time. An exemplary (novel) adhesive can have a short retention period of a few minutes to a few hours, or a longer retention period of over 9 days on skin, and have noticeably low adhesion to both hydrophilic and hydrophobic substrates. In one illustrative example, a device consisting of an exemplary (novel) adhesive-coated substrate, where the substrate was a pad, remained on the body or skin for more than 9 days. It was found, unexpectedly, that the adhesive had sufficient bonding to skin to be amenable for use in skin patches suitable under active-wear conditions involving exercise, sauna conditions, swimming, daily showers, and other physical activity for more than 9 days of continuous (long-term) wear.

In another illustrative embodiment, a patch equipped with an exemplary (novel) adhesive in accordance with the present disclosure was removable and repositionable. For example, the patch could be lifted from the skin and then repositioned on another section of the body. In so doing, the adhesive is capable of bonding and re-bonding to skin for a period of time. Illustratively, bonding, separation, and rebonding may be continued for over 5 days of wear in a moist environment, i.e., on the skin. In another example, bonding, separation, and rebonding may be continued for over 9 days of wear in a moist environment, i.e., on the skin. In many instances, a subject wearing an exemplary (novel) adhesive-coated patch or the exemplary (novel) adhesive per se experienced little or no pain upon removal of the adhesive.

Another illustrative embodiment of the present disclosure is a dermal patch having an adhesive as described herein that may be removed or moved without substantial pain to the subject or wearer. In many instances, there was no significant pain upon removal of the patch after any stage of wear and such removal did not require any special chemical or physical modification of the adhesive composition to reduce adhesion. Further, the adhesive of such a dermal patch may not leave residue upon removal and can be removed gently and painlessly at any stage of wear, i.e., after either long term or short term use.

Another illustrative embodiment of the present disclosure includes a device also having backing materials. Backing materials can provide a barrier between the substrate and the external environment and can be formed by calendar coating, hot melt coating, solution coating, etc. The backing materials can be plastic films of polyethylene, vinyl acetate resins, ethylene/vinyl acetate copolymers, polyvinyl chloride, polyurethane, and like polymers, metal foils, non-woven fabric, cloth and commercially available laminates. The backing material generally has a thickness in the range of about 2 micrometers to about 1000 micrometers and a dermal adhesive composition as described herein is generally applied to a backing material in a thickness ranging from about 12 micrometers to about 250 micrometers.

Another illustrative embodiment of the present disclosure includes a pressure-sensitive novel adhesive composition suitable for short term (i.e., a few hours) to long term (i.e., over 9 days) skin wear. The novel adhesive composition is associated with noticeably low adhesion to both hydrophilic and hydrophobic substrates, and a noticeably low level of pressure-sensitive tack. The aforementioned features lead to significant reduction in the level of pain experienced upon removal of the adhesive composition after any stage of wear. Accordingly, the composition does not require any special chemical or physical modification in order to reduce pain upon removal. Unexpectedly, an exemplary (novel) adhesive in accordance with the present disclosure bonds so effectively to skin in long term wear applications that adhesive-equipped skin patches used for extremely active wear conditions of exercise, sauna, swimming, daily showers, and other physical activity may be worn continuously for over 9 days.

Another illustrative embodiment of the present disclosure includes an exemplary (novel) adhesive as described herein having associated therewith cross-linking agents, general additive agents, an antioxidant, a light stabilizer, an age resistor, a separation adjusting agent, a plasticizer, a softening agent, a filler, a coloring agent, a surfactant, and/or an antistatic agent.

While pressure-sensitive adhesives in accordance with the present disclosure may be illustrated by means of a patch (for example), another illustrative embodiment includes the use of pressure sensitive adhesives described herein for adhering objects to skin. Illustratively, objects that may be adhered to skin include needles, tubes, sensors, leads, and/or any other object for which adherence to skin and subsequent removal with little or no pain after short term or long term wear is desired.

The disclosure will be further described in connection with the following examples, which are set forth for purposes of illustration only.

EXAMPLES

Example 1

Table 1 shows formulations of base adhesives, exemplary (novel) pressure-sensitive adhesives, and comparative adhesives. The novel pressure-sensitive adhesive compositions E-1 to E-6 contain a base acrylic polymer adhesive prepared from polymerization of acrylic acid and acrylic or meth (acrylic) esters, polyvinylpyrrolidone (PVP) or a mixture of polyvinylpyrrolidones (PVPs), and a low softening point resin blended together using a standard lab mixer.

Base adhesive samples A, B and C were prepared using unmodified, base acrylic adhesives available commercially. Base adhesive sample A was an Aroset™ 488-based medical-grade adhesive manufactured by Ashland and coated onto a 2-mil thick polyester film at a thickness of about 2 mil. Base adhesive samples B and C were prepared following the same process, but with a different base adhesive. Base adhesive sample B was made with Gelva® 2495 adhesive manufactured by Cytec Industries. Base adhesive sample C was made with Aroset™ 280 manufactured by Ashland. These samples were dried at room temperature for 5 minutes, further dried at 70° C. for 5 minutes, and then cured at 135° C. for 15 minutes. The adhesive surface of the dried and cured sample was covered by paper release liner.

Exemplary (novel) pressure-sensitive adhesive samples and comparative adhesive samples were made using adhesive formulations described in Table 1. For example, to prepare the exemplary (novel) adhesive E-1, 182 grams of Gelva® 2495 base adhesive (i.e., base adhesive B, in dry weight 82 grams) were placed in a mixing vessel with a stirrer. To the base adhesive were added the following components while stirring: 12.5 grams of a 40% solution of Acrynax 4326 resin in ethyl acetate, 25 grams of a 20% solution of Kollidon® 90F in ethanol, and 14.5 grams of a 55% solution of Kollidon® 25 in ethanol. Table 1 shows the dry weight amount of each component. The coatings for exemplary (novel) pressure-sensitive adhesive samples and comparative adhesive samples were prepared as described above for base adhesive samples A, B and C. The samples were cut to a 1-inch width for adhesion and tack testing.

TABLE 1

Adhesive Compositions

| | Base Adhesives | | | Exemplary (Novel) Adhesives | | | | | | Comparative Adhesives | | | | |
|---|---|---|---|---|---|---|---|---|---|---|---|---|---|---|
| Adhesive ID | A | B | C | E-1 | E-2 | E-3 | E-4 | E-5 | E-6 | C-1 | C-2 | C-3 | C-4 | C-5 |
| Aroset ™ 280 | — | — | 100 | — | — | — | — | 82 | — | — | — | — | — | — |
| Gelva ® 2495 | — | 100 | — | 82 | — | — | — | — | — | — | — | — | — | — |
| Aroset ™ S488 | 100 | — | — | — | 82 | 82 | 82 | — | 82 | 82 | 82 | 82 | 82 | 82 |
| Kollidon ® 25 | — | — | — | 8 | 8 | 8 | — | 8 | 4 | — | — | — | — | 8 |
| Kollidon ® 90F | — | — | — | 5 | 5 | — | 5 | 5 | 2.5 | — | — | — | 5 | — |
| Kollidon ® 12PF | — | — | — | — | — | — | — | — | — | — | — | 8 | — | — |
| Acrynax 4326 | — | — | — | 5 | 5 | 5 | 5 | 5 | 5 | 5 | 15 | — | — | — |

Example 2

This example is provided to illustrate three properties of adhesives in accordance with the present disclosure; namely, adhesion, tack and cohesive strength (also known as hold or shear strength). Exemplary devices and adhesives were tested in order to determine the influence of adhesive composition on all three of the aforementioned functional adhesive properties. These three properties are typically evaluated to characterize pressure-sensitive adhesives. A texture analyzer (TA) test was used to measure the adhesive forces associated with consecutive measurements on the same area of adhesive surface to simulate adhesive re-application.

Adhesion

Adhesion was determined using an ASTM D3330/D3330M-04 standard test method for measuring peel adhesion of pressure-sensitive tapes. This test was carried out on an Instron tensile strength testing machine. Stainless steel panels were cleaned with methyl ethyl ketone (MEK), and polypropylene panels were cleaned with isopropyl alcohol (IPA) and then dried. Each sample of adhesive was 2-mil in thickness and was applied on a 2-mil polyethylene terephthalate (PET) film. The samples were cut to have a 1-in width, applied to a panel, rolled twice with a 4.5-lb roller, and held at room temperature for 30 min. These tests, the results of which are shown in Table 2, were conducted at a 180 degrees peeling angle and at 12 in/min jar separation.

Tack

Tack was determined using an ASTM D2979-01 standard test method for measuring pressure-sensitive tack of adhesives. An inverted probe machine was used that had a type 304 stainless steel probe with a 5 mm diameter and was operated at 10 mm/s, for 1.0 s, and at a contact pressure of 9.79 kPa. The results of these tests are shown in Table 2.

TABLE 2

Adhesive Properties: Adhesion and Tack

| Property | Base Adhesives | | | Exemplary (Novel) Adhesives | | | | | Comparative Adhesives | | | | |
|---|---|---|---|---|---|---|---|---|---|---|---|---|---|
| | A | B | C | E-1 | E-2 | E-3 | E-5 | E-6 | C-1 | C-2 | C-3 | C-4 | C-5 |
| Adhesion to steel, lb/in | 8.6 | 5.0 | 4.8 | 3.8 | 2.3 | 2.8 | 2.9 | 3.1 | 7.5 | 6.0 | 6.6 | 3.0 | 4.0 |
| Adhesion to PP, lb/in | 3.0 | 3.0 | 2.8 | 2.3 | 1.0 | 0.8 | 1.3 | 0.87 | 2.4 | 1.1 | 0.5 | 2.9 | 1.5 |
| Probe tack, g | 1878 | 1246 | 1169 | 677 | 528 | 550 | 544 | 625 | 1682 | 1381 | 961 | 1000 | 700 |

Cohesive Strength

Cohesive strength was determined using an ASTM D6463/D6463M-06 standard test method for measuring the time to failure of pressure-sensitive articles under sustained shear loads. Each sample was coated on a 2-mil PET film, bonded to a stainless steel panel by rolling the sample twice with a 4.5-lb roller, and then allowed a dwell time of 30 minutes before a 500-g load was applied parallel to the bonding surface. The sample was placed in the oven at 70° C. Slippage of the sample was measured in mm. Adhesives with lower slippage have higher cohesive strength. The results of these tests, which are shown in Table 3, indicate that exemplary (novel) adhesives in accordance with the present disclosure have a range of cohesive strengths. Higher cohesive strength formulation may be useful for longer term skin wear because such formulations have more resistance to skin oils and perspiration.

TABLE 3

Adhesive Properties: Cohesive Strength at 70° C. on Steel as Slippage After 1 hr (in mm)

| Base Adhesives | | | Exemplary (Novel) Adhesives | | | | | Comparative Adhesives | | | |
|---|---|---|---|---|---|---|---|---|---|---|---|
| A | B | C | E-1 | E-2 | E-3 | E-5 | E-6 | C-1 | C-2 | C-3 | C-4 |
| 2 mm | 0 mm | 0 mm | fell off | 1 mm | 1 mm | 0 mm | 2 mm | 2 mm | fell off | fell off | 0.5 mm |

Texture Analyzer

It was found that using the texture analyzer (TA) technique demonstrated various unexpected benefits and improvements provided by exemplary (novel) adhesives in accordance with the present disclosure as compared to conventional base adhesives. A texture analyzer (TA) probe was used to measure the adhesive forces between measurements on the same area or to simulate re-application. To simulate skin in a laboratory setting, particularly its hydrophilic and hydrophobic components, separate tests conducted with an adhesive patch were performed using hydrophilic and hydrophobic TA probe surfaces. A stainless steel probe was utilized to simulate re-bonding to a hydrophilic surface (for example, skin areas with moisture or perspiration), since a steel TA probe has a high energy surface. In one set of experiments, the TA probe was not cleaned with solvent between applications to simulate patch reapplication to the same area from which it was removed.

Adhesive samples in an exemplary device, i.e., a patch, were characterized using a TA probe made by Texture Technologies Corp. The maximum force or peak force was the force required to separate the TA probe from the adhesive in the patch; the total area under the TA Force Time curve was measured to determine the total energy required to break the adhesive bond with the TA Probe. Two types of TA probe were used: a stainless steel probe and a polypropylene (PP) probe. A 5-kg TA load cell was used with the following settings: pre-test speed 1.0 mm/s, test speed 0.1 mm/s, and post-test speed 0.5 mm/s. The TA probe was pressed into an adhesive with a 150-g force, and the TA probe was then moved up to separate the adhesive from the probe. The TA curves (force vs. time) were obtained, and the peak force and the area under TA curve were calculated.

FIG. 1A shows peak force data recorded for an exemplary (novel) adhesive-equipped device (i.e., a patch) that has been applied, removed, and reapplied to the same place on a steel probe, which probe was not cleaned between applications. The steel probe TA data showed that whereas an exemplary (novel) adhesive in accordance with the present disclosure retains its peak force, a conventional adhesive loses its peak-force after multiple re-applications.

Figure 1B:
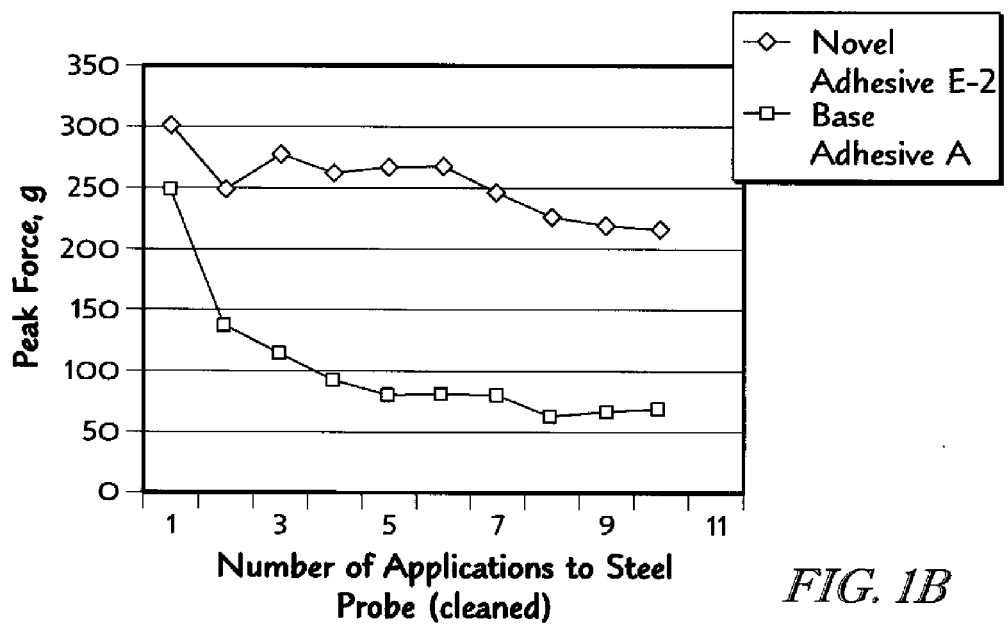
FIG. 1B is a graph showing peak force data recorded for an exemplary (novel) adhesive-bearing device that has been reapplied multiple times onto a steel probe the surface of which has been cleaned between each consecutive application.

FIG. 1B shows peak force data recorded for an exemplary (novel) adhesive-equipped device (i.e., a patch) that has been applied, removed, and reapplied to different places on a steel probe, which probe was cleaned between applications. The steel probe TA data again showed that whereas an exemplary (novel) adhesive in accordance with the present disclosure retained its peak force, a conventional adhesive loses its peak-force after multiple re-applications. As shown in Table 4, the percent peak force retention is lower for re-application to a cleaned surface thereby supporting the proposition that an adhesive may leave a residue on a surface, which residue may serve as a primer allowing easier re-bonding after application.

TABLE 4

% TA Peak Force Retention After 10 Consecutive Applications

| Test Mode | Description of Adhesive | % Force Retention |
|---|---|---|
| Probe cleaned with MEK before each reapplication | Exemplary (Novel) Adhesive E-2 | 71 |
| Probe cleaned with MEK before each reapplication | Base Adhesive A | 23 |
| Probe not cleaned before each reapplication | Exemplary (Novel) Adhesive E-2 | 95 |
| Probe not cleaned before each reapplication | Base Adhesive A | 33 |

Figure 2:
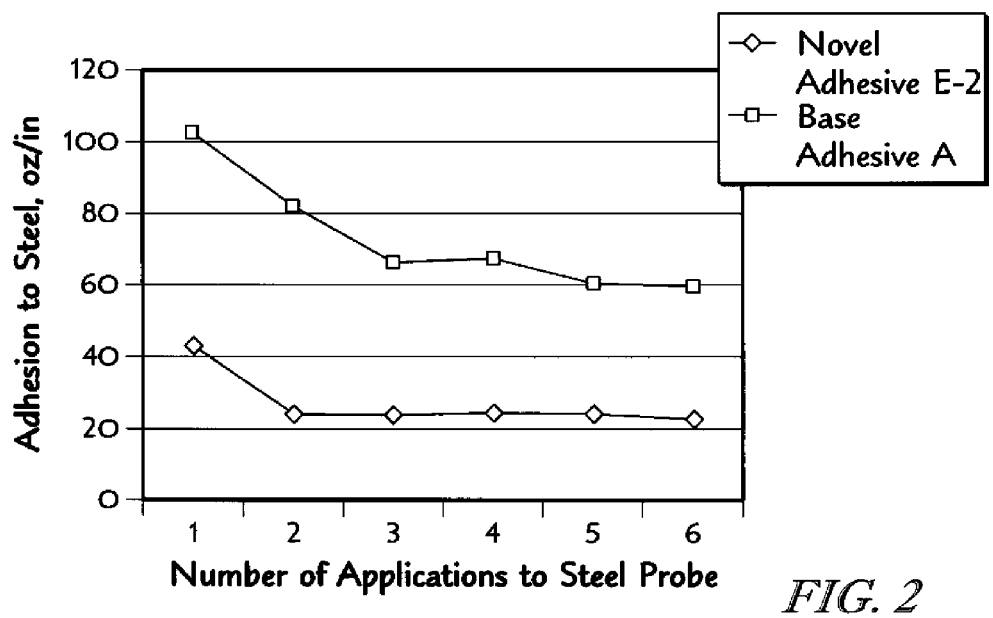
FIG. 2 is a graph showing the retained adhesion of an exemplary (novel) adhesive on a steel surface.
Figure 3:
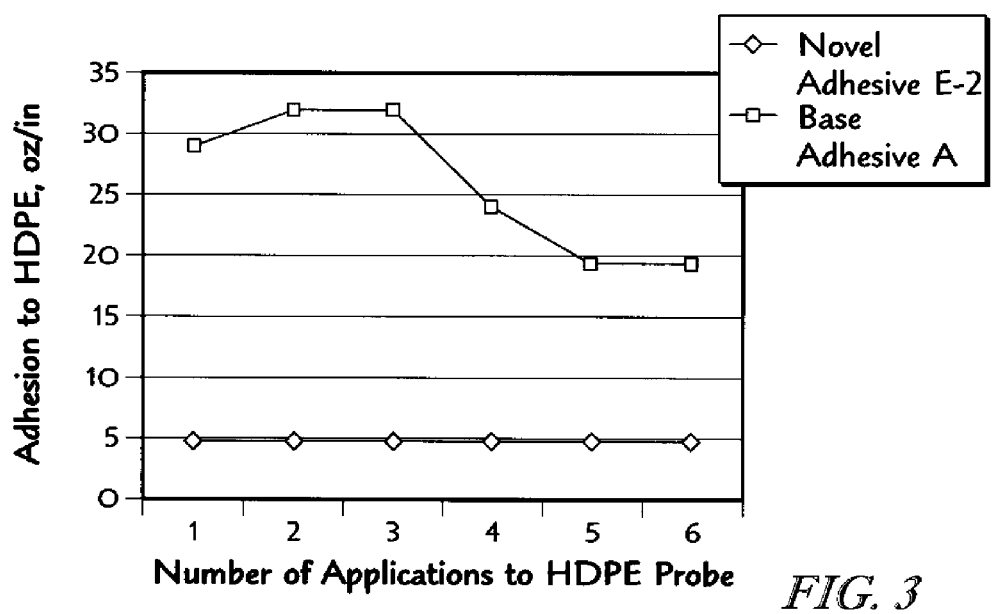
FIG. 3 is a graph showing the retained adhesion of an exemplary (novel) adhesive on a high density polyethylene (HDPE) surface.
Figure 4:
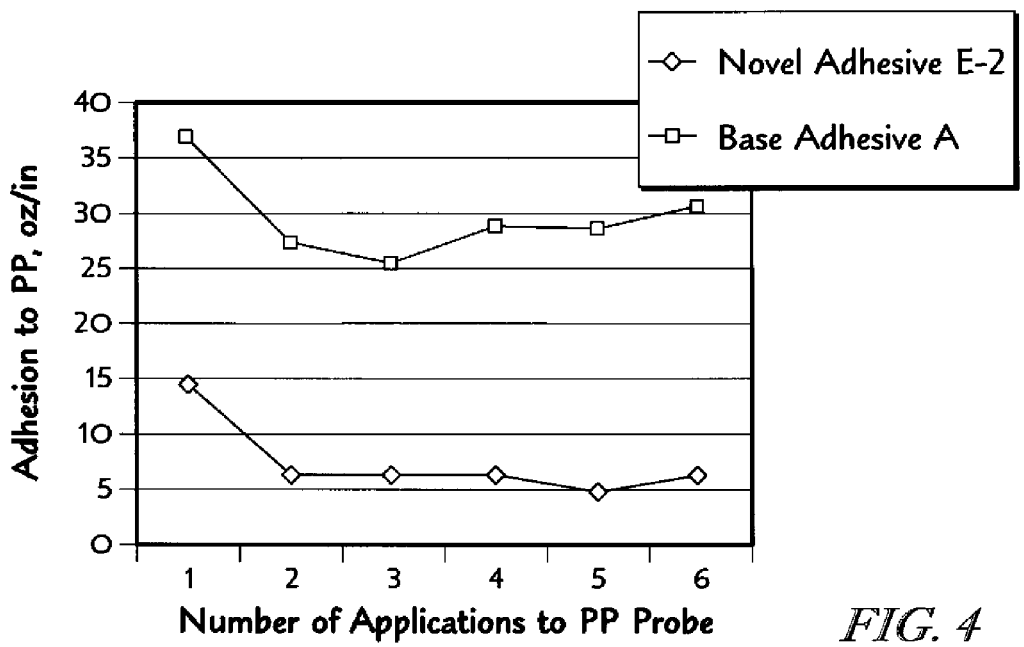
FIG. 4 is a graph showing the retained adhesion of an exemplary (novel) adhesive on a polypropylene (PP) surface.

FIGS. 2, 3, and 4 are graphs showing the retained adhesion, as a function of the number of applications, of a patch equipped with an exemplary (novel) adhesive or a comparative (conventional) adhesive on stainless steel, HDPE, and PP surfaces, respectively. Initial adhesion to a surface (e.g., adhesion to steel per ASTM D3330/D3330M) and 180 degree peeling at 12 in/min was measured by application and reapplication of a sample to the same place on the surface up to 10 times to simulate re-positionability. The adhesion (as tested on steel, HDPE and PP probes) of an exemplary (novel) adhesive over time was significantly lower compared to the adhesion of a comparative (conventional) adhesive. Lower adhesion values to both hydrophilic and hydrophobic surfaces can be beneficial, since lower adhesion would be expected to correlate with reduced pain during removal of an adhesive or removal of a patch equipped with the adhesive from skin. Test data shown in Table 3 and Table 5 support this correlation.

TABLE 5

Cohesive Strength at 70° C. on Steel as Slippage After 1 hr (in mm) and Scaled Pain Level Upon Adhesive Removal: 0 = No Noticeable Pain, 5 = Notable Pain

| Base Adhesives | | | Exemplary (Novel) Adhesives | | | | | Comparative Adhesives | | | |
|---|---|---|---|---|---|---|---|---|---|---|---|
| A | B | C | E-1 | E-2 | E-3 | E-5 | E-6 | C-1 | C-2 | C-3 | C-4 |
| 2 mm | 0 mm | 0 mm | fell off | 1 mm | 1 mm | 0 mm | 2 mm | 2 mm | fell off | fell off | 0.5 mm |
| 5 | 4 | 4 | 1 | 0 | 1 | 1 | 2 | 5 | 5 | 4 | 3 |

Example 3

Table 6 shows dynamic mechanical analysis (DMA) data for exemplary (novel) and comparative (conventional) adhesives, which data reflect the modulus (stiffness) and damping (energy dissipation) properties of materials as they are deformed under dynamic stress. These measurements provide quantitative information about the performance of materials. The DMA results showed that exemplary (novel) adhesive E-2 has a significantly higher complex modulus, G*, and a slightly higher glass transition temperature, Tg, compared to base adhesive A. Individual components exert different effects on the rheological properties of base adhesive A. Addition of PVP results in a harder adhesive, as evident from an increase in G*, a decrease in tan delta, and an increase in Tg. However, addition of low softening point resin resulted in a slight shift in Tg to a lower temperature and an increase in tan delta with a slight decrease in G*.

Overall, a modified adhesive, i.e., an exemplary (novel) adhesive, was harder, which is consistent with a decreased level of adhesion and correlates with reduced pain during removal from skin as shown in Table 3 and Table 5.

TABLE 6

Dynamic Mechanical Analysis (DMA) Data for Exemplary (Novel) and Comparative Adhesives

| Adhesive | Adhesive Composition | Tg (° C.) | G* (kPa) @ 50° C. | tan delta @ 50° C. |
|---|---|---|---|---|
| A | Aroset ™ S488 | −22.4 | 12.5 | 0.61 |
| E-2 | Aroset ™ S488 modified with high and low MW PVP and Acrynax resin | −20.5 | 35.4 | 0.61 |
| C-1 | Aroset ™ S488 with 5 parts dry weight Acrynax resin | −24.1 | 10.5 | 0.76 |
| C-2 | Aroset ™ S488 with 15 parts dry weight Acrynax resin | −24.8 | 12.8 | 0.77 |
| C-5 | Aroset ™ S488 with low MW PVP (Kollidon ® 25) | −16.6 | 52.4 | 0.61 |

TABLE 6-continued

Dynamic Mechanical Analysis (DMA) Data for Exemplary (Novel) and Comparative Adhesives

| Adhesive | Adhesive Composition | Tg (° C.) | G* (kPa) @ 50° C. | tan delta @ 50° C. |
|---|---|---|---|---|
| C-4 | Aroset ™ S488 with high MW PVP (Kollidon ® 90F) | −22.3 | 39.2 | 0.43 |

Example 4

Figure 5:
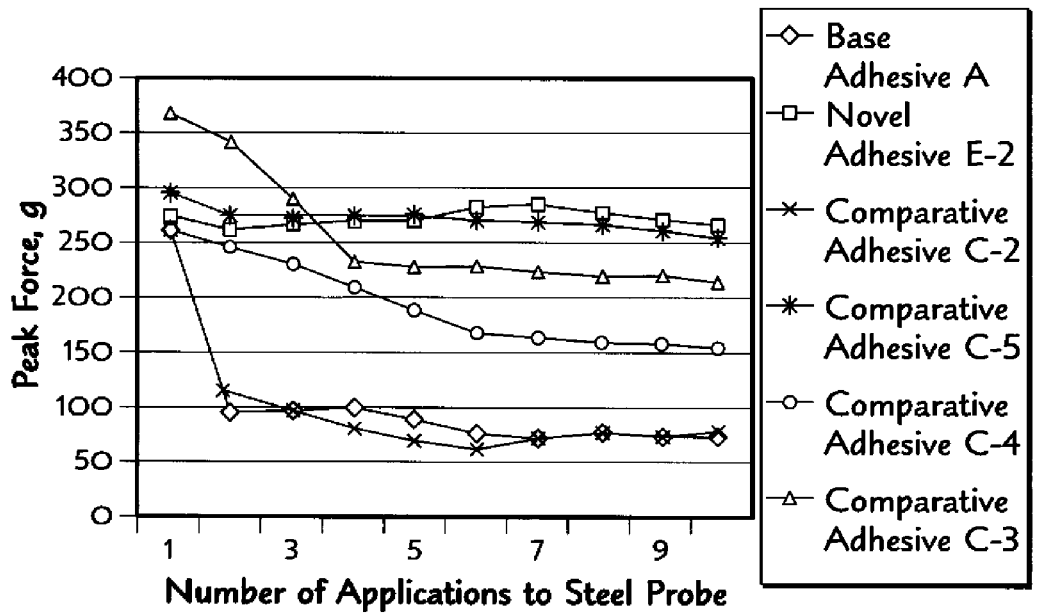
FIG. 5 is a graph showing peak force steel retention data recorded for an exemplary (novel) adhesive and for comparative adhesives as a function of the type of polyvinylpyrrolidone (Kollidon®) used in the adhesive formulation.

FIG. 5 shows the effect of PVP grade on peak force retention as illustrated by comparative adhesives C-3, C-4 and C-5. Mid-molecular weight PVP Kollidon® 25 has a stronger effect on peak force retention leading to improved re-bonding in comparison to higher molecular weight PVP Kollidon® 90F, or lower molecular weight Kollidon® 12PF. The data in FIG. 5 were obtained from a texture analyzer using a steel probe and a Peltier Plate set up at 50° C. to compensate for heat loss in testing. This test was conducted at an elevated temperature to approximate normal body temperature, which is about 36° C. It was also found that the level of pain experienced during removal of an adhesive from skin varied for different PVP grades, e.g., Kollidon® 25 provided better and more gentle removal when added alone or in combination with other components (see, Table 5).

Example 5

Figure 6:
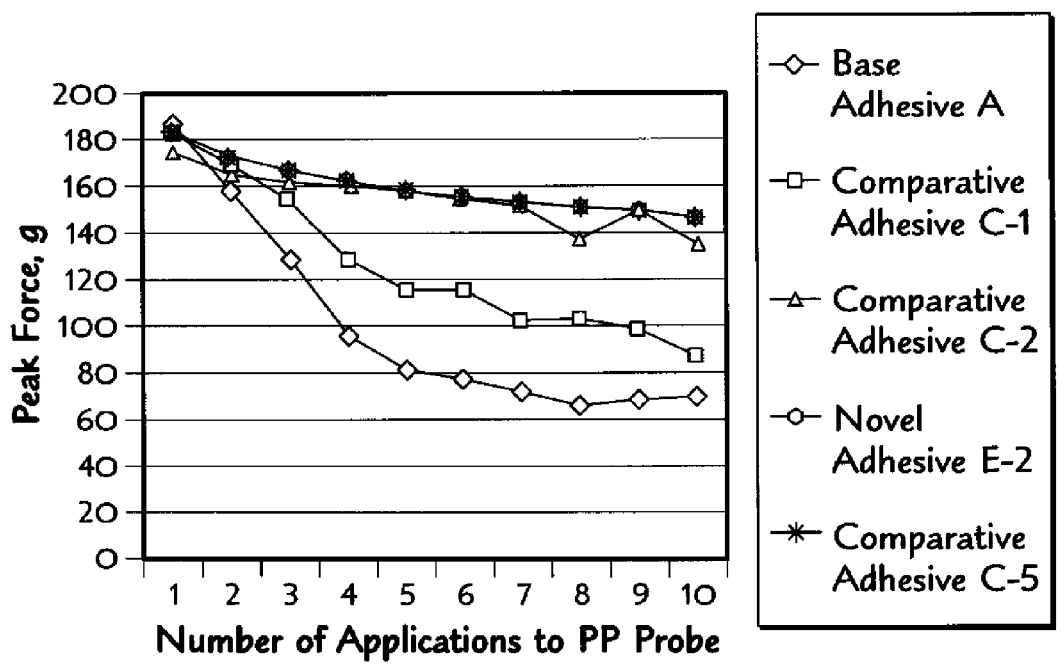
FIG. 6 is a graph showing peak force PP retention data recorded for an exemplary (novel) adhesive and for comparative adhesives as a function of the amount of a low softening point resin (Acrynax) used in the adhesive formulation.

A low softening point resin (Acrynax) was used to formulate exemplary and comparative adhesives exhibiting lower peak force. FIG. 6 shows peak force data illustrating low softening point resin influence (Acrynax) on peak force retention after re-application to hydrophobic surfaces. As illustrated by comparative adhesives C-1 and C-2 in FIG. 6, the addition of Acrynax did not diminish peak force retention for PVP-containing formulae tested using a PP probe.

Figure 7:
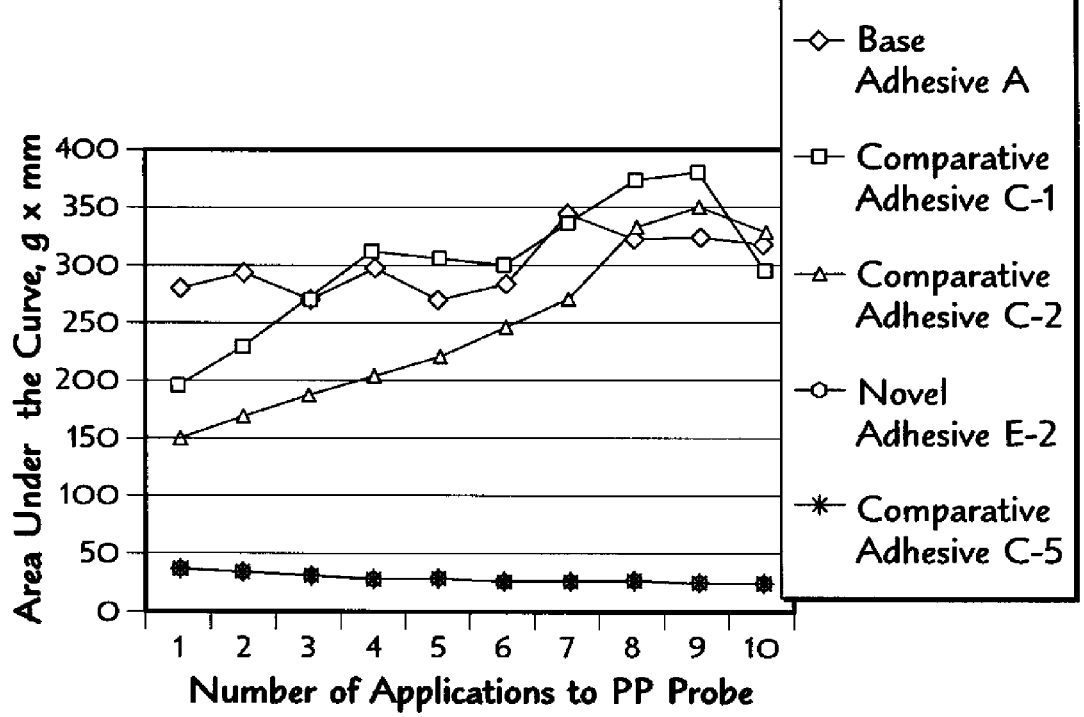
FIG. 7 is a graph showing that the area under the curve obtained in a texture analyzer (TA) test using a PP probe varies with reapplication of adhesives depending on whether polyvinylpyrrolidone (Kollidon®) and low softening point resin (Acrynax) are used in the adhesive formulation.

FIG. 7 shows the effect of Acrynax resin on the area under the curve obtained in TA tests using a PP probe. The area under the TA curve was observed to increase with reapplication of comparative adhesives C-1 and C-2 containing Acrynax resin. The area under the curve did not increase with re-application of comparative adhesive C-5 without the Acrynax low softening point resin, which adhesive contains only PVP, nor did the area under the curve increase with re-application of exemplary (novel) adhesive E-2, which adhesive contains PVP and Acrynax resin. Without wishing to be bound by theory, Acrynax is believed to increase the re-bonding ability of an adhesive by means of increasing the total energy required to break the bond with hydrophobic surfaces, thereby mimicking application of an adhesive to hydrophobic components of the skin.

Conventional, i.e., comparative, adhesives exhibited noticeably high initial adhesion levels to steel, HDPE and PP, and significant decreases in adhesion to steel and HDPE after re-application. Upon introduction of one or more PVPs and Acrynax resin, exemplary (novel) adhesives displayed adhesion and tack levels that did not change significantly after re-application and which are well below levels associated with conventional long term wear adhesives. This effect is expected to provide significant reduction in pain upon removal while providing sufficient bonding to skin so as to be compatible for use in skin patches destined for extremely active wear for over 7 days of continuous use.

Although only a number of exemplary embodiments of the present disclosure have been described in detail above, those skilled in the art will readily appreciate that many modifications are possible in the exemplary embodiments without materially departing from the novel teachings and advantages. Accordingly, all such modifications are intended to be included within the scope of this disclosure as defined in the following claims.

As used in the specification and the appended claims, the singular forms "a," "an" and "the" include plural referents unless the context clearly dictates otherwise. Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

Throughout the description and claims of this specification, the word "comprise" and variations of the word, such as "comprising" and "comprises," means "including but not limited to," and is not intended to exclude, for example, other additives, components, integers or steps. "Exemplary" means "an example of" and is not intended to convey an indication of a preferred or ideal embodiment. "Such as" is not used in a restrictive sense, but for explanatory purposes.

Disclosed are components that can be used to perform the disclosed methods and prepare the disclosed materials. These and other components are disclosed herein, and it is understood when combinations, subsets, interactions, groups, etc. of these components are disclosed that while specific reference of each various individual and collective combinations and permutation of these may not be explicitly disclosed, each is specifically contemplated and described herein, for all methods and materials. This applies to all aspects of this application including, but not limited to, steps in disclosed methods. Thus, if there are a variety of additional steps that can be performed, it is understood that each of these additional steps can be performed with any specific embodiment or combination of embodiments of the disclosed methods.

It will be apparent to those skilled in the art that various modifications and variations can be made without departing from the scope or spirit of the present disclosure. Other embodiments will be apparent to those skilled in the art from consideration of the specification and practice disclosed herein. It is intended that the specification and examples be considered as exemplary only.

The invention claimed is:

1. An adhesive comprising:
   a) about 60% to 94% by weight of an acid-functionalized polyacrylate, wherein the polyacrylate comprises monomers of acrylic acid and acrylic or meth(acrylic) esters,
   b) about 3% to 20% by weight of one or more polyvinylpyrrolidones, and
   c) about 5% to 20% by weight of a low softening point resin, wherein the resin has a glass transition temperature below minus 30° C.

2. The adhesive of claim 1, wherein the polyacrylate is present in about 70% to 80% by weight.

3. The adhesive of claim 1, wherein the one or more polyvinylpyrrolidones are present in about 5% to 10% by weight.

4. The adhesive of claim 3, wherein the adhesive comprises one polyvinylpyrrolidone.

5. The adhesive of claim 4, wherein the polyvinylpyrrolidone has a weight average molecular weight of about 2,000 g/mol to 3,000 g/mol.

6. The adhesive of claim 4, wherein the polyvinylpyrrolidone has a weight average molecular weight of about 28,000 g/mol to 34,000 g/mol.

7. The adhesive of claim 4, wherein the polyvinylpyrrolidone has a weight average molecular weight of about 1,000,000 g/mol to 1,500,000 g/mol.

8. The adhesive of claim 3, wherein the adhesive comprises more than one polyvinylpyrrolidone.

9. The adhesive of claim 1, wherein the low softening point resin is a copolymer of acrylamide and ethylhexyl acrylate.

10. The adhesive of claim 1, wherein the adhesive at about a 2 mil thickness has an adhesion value to steel between about 0.2 lb/linear inch and 4.0 lb/linear inch.

11. The adhesive of claim 1, wherein the adhesive at about a 2 mil thickness has an adhesion value to polypropylene between about 0.2 lb/linear inch and 1.5 lb/linear inch.

12. The adhesive of claim 1, wherein the adhesive at about a 2 mil thickness has an adhesion value to steel of less than 4.0 lb/linear inch.

13. A device approved for medical application comprising a coating of the adhesive of claim 1.

14. The device approved for medical application of claim 13, wherein the adhesive is directly coated or transfer coated onto the device.

15. The device approved for medical application of claim 14, wherein the device is selected from the group consisting of a pad, film, foam, carrier, and substrate that is approved for medical application.

16. The adhesive of claim 1, wherein the polyacrylate is a pressure-sensitive acrylic polymer.

17. The adhesive of claim 16, wherein the adhesive is able to re-bond to hydrophilic and hydrophobic surfaces for a period of over 9 days.

18. The adhesive of claim 16, wherein the adhesive has a viscosity ranging from about 1,500 to about 25,000 centipoise at ambient temperature as a solvent-based composition.

* * * * *